(12) United States Patent
Moon et al.

(10) Patent No.: US 8,298,394 B2
(45) Date of Patent: Oct. 30, 2012

(54) NON-GEL BASED TWO-DIMENSIONAL PROTEIN SEPARATION MULTI-CHANNEL DEVICES

(75) Inventors: Myeong Hee Moon, Gyeonggi-do (KR); Ki Hun Kim, Seoul (KR)

(73) Assignee: Yonsei University—Industry Academic Cooperation Foundation, Seoul (KR)

( * ) Notice: Subject to any disclaimer, the term of this patent is extended or adjusted under 35 U.S.C. 154(b) by 463 days.

(21) Appl. No.: 12/531,281

(22) PCT Filed: May 25, 2009

(86) PCT No.: PCT/KR2009/002742
§ 371 (c)(1),
(2), (4) Date: Sep. 14, 2009

(87) PCT Pub. No.: WO2009/145532
PCT Pub. Date: Dec. 3, 2009

(65) Prior Publication Data
US 2011/0253535 A1    Oct. 20, 2011

(30) Foreign Application Priority Data
May 26, 2008   (KR) ......................... 10-2008-0048842

(51) Int. Cl.
*B01D 57/02*   (2006.01)
(52) U.S. Cl. ........................ 204/644; 204/548; 204/459
(58) Field of Classification Search .......... 204/451–455, 204/459, 600–605, 610, 644, 548; 435/7.1, 435/287.2, 283.1, 288.5; 422/99, 100, 72, 422/63, 64, 502
See application file for complete search history.

(56) References Cited

FOREIGN PATENT DOCUMENTS
KR        0109008 A   11/2007
KR        0109008 A   11/2007

OTHER PUBLICATIONS

Kang et al. (2006) Anal. Chem, 78:5789-5798, "Development of non-gel-based two-dimensional separation of intact proteins by an on-line hyphenation of capillary isoelectric focusing and hollow fiber flow field-flow fractionation".
Oh et al. (2007) J. Sep. Sci., 30:1082-1087, "Miniaturized asymmetrical flow field-flow fractionation: application to biological vesicles".
Oh et al. (2006) Yonsei University, Department of Chemistry, Korean with English Abstract.

*Primary Examiner* — Alex Noguerola
*Assistant Examiner* — Gurpreet Kaur
(74) *Attorney, Agent, or Firm* — Swanson & Bratschun, L.L.C.

(57) ABSTRACT

Provided is a multi-channel apparatus for non-gel based two-dimensional protein separation. One or more flat channels are arranged in parallel and have an isoelectric focusing section for primarily separating proteins from protein samples according to isoelectric point (pI) and a flow field-flow fractionation section for secondarily separating the primarily separated proteins according to molecular weight, thereby making it possible to simultaneously separate the proteins in multiple channels, to increase a protein separation speed, and to overcome limitation to sample injection due to an increase in channel volume. The apparatus can separate the proteins according to pI and molecular weight, be safe from denaturation of the protein in the process of protein separation, automatically remove an ampholyte used for pI-based separation, and separately detecting the separated proteins to identify the proteins using nanoflow liquid chromatography-electrospray ionization-tandem mass spectrometry (LC-ESI-MS-MS).

26 Claims, 7 Drawing Sheets

NON-GEL BASED TWO-DIMENSIONAL PROTEIN SEPARATION MULTI-CHANNEL DEVICES

CROSS-REFERENCE TO RELATED APPLICATIONS

This application is a 35 U.S.C §371 of PCT Application Serial No. PCT/KR2009/002742, filed May 25, 2009, currently pending, entitled "Non-gel Based Two-dimensional Protein Separation Multi-channel Devices," which claims priority to Korean Patent Application No. 10-2008-0048842 filed May 26, 2008, entitled "Non-gel Based Two-dimensional Protein Separation Multi-channel Devices," which are each incorporated herein by reference in their entirety.

TECHNICAL FIELD

The present invention relates to a non-gel based two-dimensional protein separation multichannel devices, and more particularly, to a non-gel based two-dimensional protein separation multichannel devices including one or more flat channels arranged in parallel which include an isoelectric focusing section for primarily separating proteins from protein samples according to isoelectric point (pI) and a flow field-flow fractionation section for secondarily separating the primarily separated proteins according to molecular weight, thereby making it possible to simultaneously separate the proteins in multiple channels, to increase a protein separation speed, and to overcome a limitation on sample injection due to an increase in channel volume.

BACKGROUND ART

In life science and medical applications, there is a need for systematic analysis of disease-related proteins in connection with treatment and prevention of diseases. In particular, with the development of basic research for medicine discovery including molecular biology and genomics (genome science), regions for drug discovery have recently been subjected to a rapid change, and novel methods of drug discovery representative of genomic drug discovery have been developed.

As such, in life science and medical applications for developing novel pharmaceutical drugs, substances having physiological activity in specific diseases or environments must be checked. Most of the biological substances are composed of protein, and explanation of structure and function of the protein falls under basic issues in life science and medical applications. In particular, about 35,000 kinds of human genes have been identified, but the number of proteins produced by genomes is estimated to range from hundreds of thousands to several millions. Since the proteins are involved in all necessary reactions within cell organelle, it is necessary to systematically conduct research on functions of genes at the level of proteins.

Meanwhile, the proteins are very complicated due to various properties such as a molecular weight, isoelectric point (pI), hydrophilicity, hydrophobicity, and so on. Thus, in order to analyze the proteins, it is necessary to primarily separate the proteins, and then to indentify the separated proteins in connection with mass spectrometry, bioinformatics, and so on. In this process, disease-related proteins are relatively smaller than the other sound proteins, it is necessary to analyze the proteins using high-performance protein separation technology. In particular, the proteins are very important to life activities, and represent their functions in interaction with other molecules including protein molecules, DNA molecules, synthetic compounds or photons. For this reason, in order to understand specific proteins, which interaction occurs along with any molecule is examined by identifying molecules having an influence on each other and by explaining a mechanism of the interaction (physiological action), instead of being limited to merely specifying the physical and/or chemical properties of these molecules.

A typical method of separating and analyzing the proteins is sodiumdodecylsulfate-polyacrylamide gel electrophoresis (SDS-PAGE), in which the proteins are separated due to a difference in selectivity by applying an electric field to a polyacrylamide gel plate. This method is a one-dimensional separation method that is widely used in the field of separating and identifying proteins in order of molecular weight and in the process of separating and identifying simple proteins, and has a problem in that the proteins have a tertiary structure denatured in an SDS solution, or are confined in the gel.

Meanwhile, the proteins produced by a genome are genetically defined as a proteome. When many protein mixtures including the proteome, in which generation, relative abundance, etc. of the protein are determined depending on an intracellular position or the physiological state of a cell or an organ, are separated, and then properties of the protein mixtures are identified, the identification itself is impossible using the aforementioned one-dimensional separation technology alone. Thus, in order to separate the protein mixtures, a two-dimensional (2D) separation method called 2D-polyacrylamide gel electrophoresis (2D-PAGE) is used, in which the proteins, which are primarily separated according to the protein property, are secondarily separated according to the molecular weight of the protein [Zhou, F. et al. *Anal. Chem.* 2004, 76, pp. 2734-2740; Klose, J. et al. *Electrophoresis*, 1995, 16, pp. 1034-1059; Righetti, P. G.1 et al. "Prefractionation Techniques in Proteome Analysis," *Anal. Chem.* 2001, 73, pp. 320-326]. In this 2D-PAGE, the proteins are subjected to isolectric focusing (IEF) in a narrow gel strip, i.e. an ampholyte carrier, in which a pH gradient is fixedly formed, according to isoelectric point (pI). This process requires about 12 hours or more.

Next, the proteins are separated in order of the pI. Subsequently, the gel strip is fixed on the upper end of a polyacrylamide gel plate in a transverse direction, and then the proteins are subjected to electrophoresis in a longitudinal direction. Thereby, the proteins are separated in the longitudinal direction according to the order of size, i.e. molecular weight. At this time, the proteins having low molecular weight mainly move to a lower end of the polyacrylamide gel plate. A total time required for the 2D-PAGE separation amounts to about 36 hours. After the 2D separation is terminated, protein spots shown on the polyacrylamide gel plate are dyed, thereby checking the number of proteins. If necessary, the protein of each spot is recovered, decomposed by an enzyme, and identified using mass spectroscopy.

This 2D-PAGE is very useful in checking a rough pattern of the proteins due to its high resolution. Further, the 2D-PAGE allows the proteins to be separated on a semi-preparative scale, so that it can be used for analysis of human plasma proteins having the shape of a very complicated protein mixture as well as proteins extracted from urine, various biologic tissues, etc., and clinical detection and diagnosis of diseases [Giddings, J. C., Unified Separation Science, John Wiley & Sons, New York 1991, pp. 126-128].

However, the 2D-PAGE is a labor-intensive method, is difficult to automate, and is limited in detection sensitivity and dynamic range. Further, separating the proteins without denaturation is difficult in the 2D-PAGE because the SDS solution is used to separate the proteins, which results in separation of the proteins in the denatured state, and recovering the sample is not easy because the separated proteins are also confined in a gel matrix. As such, the 2D-PAGE must usually decompose the proteins in the gel using the enzyme, and recover and analyze the proteins in a peptide form.

Meanwhile, a capillary isoelectric focusing (CIEF) method is a method involving filling ampholyte carriers in silica capillaries along with proteins, applying an electric field to separate the proteins according to pI of the protein [Conti, M. et al. *Electrophoresis* 1996, 17, pp. 1485-1491]. Here, in comparison with the IEF of the 2D-PAGE, the CIEF is the same in principle, but different in that it uses the silica capillaries rather than the gel strip. The CIEF can be used to process a small quantity of protein samples due to the intracapillary separation, and to separate the proteins having a slight difference of 0.003 between their pI values when it has high sensitivity [Quigley, W. C. et al. *J. Anal. Chem.* 2000, 76, pp. 4645-4658]. Further, despite the capability of processing the small quantity of protein samples due to the intracapillary separation and the high sensitivity, the CIEF is limited in its separation capability to process complicated protein mixtures such as proteome. In order to increase separation efficiency, an attempt has recently been made to use the CIEF in on-line connection with a secondary separation method such as chromatography rather than as a single analysis technique.

A typical example of the technology that carries out the 2D separation in on-line connection with the CIEF is CIEF-reversed phase liquid chromatography (RPLC) that connects the CIEF with the RPLC on line. The CIEF-RPLC secondarily separates proteins or peptide bands, which are separated by pI regions in the CIEF, in a chromatography column according to hydrophobicity difference between peptides [Chen, J. et al. *Electrophoresis* 2002, 23, pp. 3143-3148]. With the use of this method, a result of conducting a test with peptide mixtures obtained by hydrolyzing the proteome of a fruit fly, *Drosophila melanogaster*, was that a peak capacity of more than 1800 could be obtained through separation of about 8 hours.

Further, CIEF-capillary gel electrophoresis (CGE) connecting the CIEF with the CGE on line can be used to carry out separation in capillaries filled with a polyacrylamide gel instead of the aforementioned polyacrylamide gel plate according to molecular weight, and attempt to separate simple proteins such as hemoglobin [Yang, C.1 et al. *Anal. Chem.* 2003, 75, pp. 215-218]. The CIEF-CGE is useful in separating peptide mixtures, which are obtained by hydrolyzing proteins with protein enzymes, rather than the proteins. However, due to protein chain breakdown occurring when the proteins pass through the chromatography column, protein loss within the chromatography column, and so on, it is difficult to apply the CIEF-CGE to the proteins. The CIEF-RPLC may be connected on line with a mass spectrometer using electrospray ionization (ESI) [Tnag, Q. et al. *Anal. Chem.* 1996, 68, pp. 2482-2487; Yang, L. et al. *Anal. Chem.* 1998, 70, pp. 3235-3241; Martinovi, S. et al. *Anal. Chem.* 2000, 72, pp. 5356-5360]. However, because the ampholyte used for the CIEF separation is not removed, the CIEF-RPLC must be subjected to separate purification in order to remove the ampholyte after the CIEF separation. As such, sample analysis is difficult in the CIEF-RPLC due to inhibition of ions in the solution without previous removal of the ampholyte. In order to solve this problem, the ampholyte must be considerably removed using membranes such as microdialyzable cathode cells [Zhou, F. et al. *Anal. Chem.* 2004, 76, pp. 2734-2740]. However, although the CIEF-RPLC is used to separate the proteins, denaturation of the proteins cannot be avoided due to use of an organic solvent during the RPLC separation, and the CIEF-RPLC cannot be applied to the separation of the proteins having large molecular weight.

Meanwhile, an example of the method of separating the proteins according to the order of molecular weight is flow field-flow fractionation (FlFFF), which is a type of field flow fractionation (FFF). The FIFFF is a separation analysis technique that is used for size-based separation of proteins, cells, water-soluble polymers, and nano-particles, as well as property analysis of a diffusion coefficient, particle size, molecular weight, and so on etc. [J. C. Giddings, et al. *Science* 1976, 193, p. 1244; M. H. Moon, et al. *Anal. Chem.* 1999, 71(14), p. 2657]. In the FFF-based separation, an available channel is a channel that has a cuboidal cross section and a hollow space. Further, because there is no stationary phase, samples are separated depending on the strength of an external field applied in a direction perpendicular to the flow of a fluid moving the samples along a channel axis. Thus, the FIFFF uses a cross flow of the fluid, and controls retention of macromolecules such as proteins by regulating a flow rate of the cross flow.

The retention of the samples in the FIFFF channel is caused by a balance between the flow rate of the cross flow flowing out through a channel bottom and Brownian diffusion of the samples. In the case of the proteins, an average height of the samples moving in the channel is determined by a degree of the Brownian diffusion which varies depending on molecular weight or a Stoke's diameter. The smaller the molecular weight, the greater the diffusion. Thus, the diffusion and the flow rate of the cross flow are balanced at a position where the proteins are distant from the channel bottom. At this time, a separation flow flowing along a channel axis is a parabolic shape, and the proteins and the macro-molecule samples are separated according to size. Accordingly, the samples having low molecular weight are discharged from the channel, so that the samples are separated according to the size of molecular weight.

Figure 1:
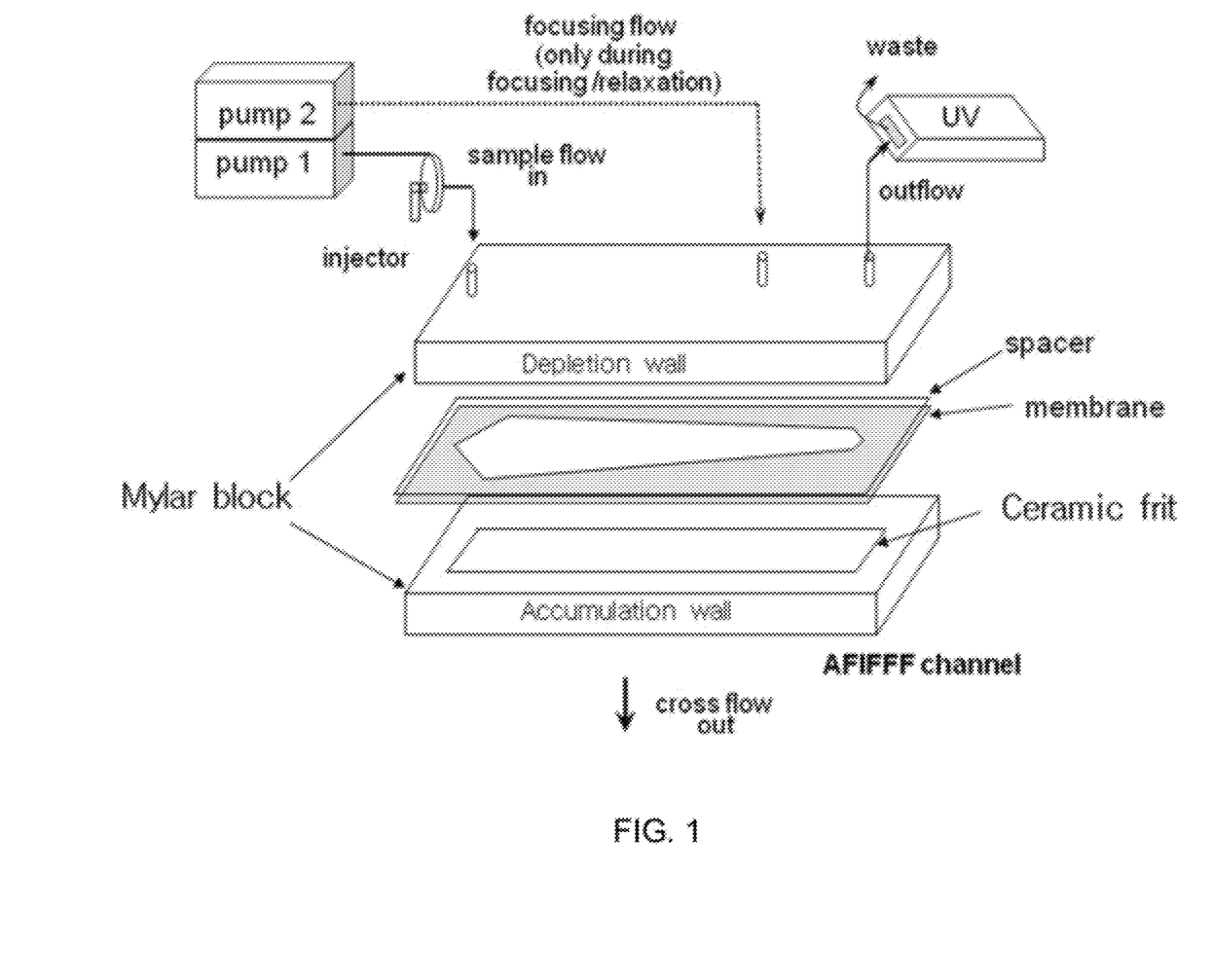
FIGS. 1 and 2 show the channel structure of a convention protein separating apparatus.

FIG. 1 shows the configuration of a flow field-flow fractionation (FIFFF) system applied to separation of proteins. An available channel is called an AFIFFF (asymmetrical flow field-flow fractionation) channel. This channel has an asymmetrical channel structure in which only a lower block under a channel has a frit, unlike a conventional symmetrical channel structure in which upper and lower blocks of a channel have respective frits. A fluid is transferred from a high performance liquid chromatography (HPLC) pump, and protein samples separated and eluted in the channel are detected using an ultraviolet/visible radiation (UV/VIS) detector. The proteins are separated in the AFIFFF channel as follows. The protein samples injected into the channel through an injector are subjected to a sample relaxation-focusing process before the separation is initiated. This sample relaxation-focusing process serves to put the samples in equilibrium between the strength of an external field applied outside the samples and diffusion of the samples, and is an essential process for the AFIFFF. The sample relaxation-focusing is carried out by injecting the fluid through an inlet of the channel as well as an outlet of the channel or an inlet of a focusing flow as in FIG. 1 to adjust a ratio of flow rates of the two flows such that the samples injected into the channel can be focused at a position corresponding to a triangular base of the channel inlet. Usually, this sample relaxation-focusing is experimentally applied by computing a ratio of a position where the samples are subjected to relaxation and focusing to an entire length of the channel to calculate the flow rate ratio. For example, the flow rate ratio may be finally determined by injecting a material such as organic dye, water-soluble ink, or the like to check a position where the material is focused. The sample relaxation-focusing requires a sufficient time for a buffer solution corresponding to a volume of the channel to flow out through the channel bottom. When the sample relaxation-focusing process is completed, inflow of the focusing flow is interrupted, and the fluid is transferred only to the channel inlet. At this time, a ratio of a cross flow flowing out through the channel bottom to an outlet flow transferred to a detector is adjusted. Thereby, the proteins are separated. In the case where the focusing flow is adjusted in such a manner that a part thereof can flow into the detector during the sample relaxation-focusing and be transferred by the flow rate of the outlet flow used when the proteins are separated, a phenomenon in which the flow of the fluid comes to a standstill at the detector can be avoided when the relaxation-focusing process is transited to the separation process.

In the FIFFF using the asymmetrical channel, when the proteins are separated, the proteins can be separated in order from low molecular weight to high molecular weight. Because the separation solution uses the buffer solution, the proteins are separated without denaturation. Because no filler is filled in the channel, risks such as breakdown of the protein samples or blocking of the separation channel can be minimized. When thickness and width of a spacer determining the volume of the channel are adjusted, the flow rate of the fluid, separation efficiency, etc. can be varied, and the proteins can be separated at a micro flow rate, which is suitable to separate a very small amount of proteins [D. Kang, M. H. Moon, *Anal. Chem.* 2004, 76, pp. 3851-3855; S. Oh et al. *J. Separation Sci.*, 2007, 30, pp. 1982-1087].

In comparison with the gel electrophoresis, the separation method using the AFIFFF can be used to separate the proteins in order from low molecular weight to high molecular weight, and minimize the breakdown of the protein samples or the blocking of the separation channel. However, the separation method using the AFIFFF is not very high in separation capability, and has difficulty in carrying out the separation on the basis of various properties of the protein.

Figure 2:
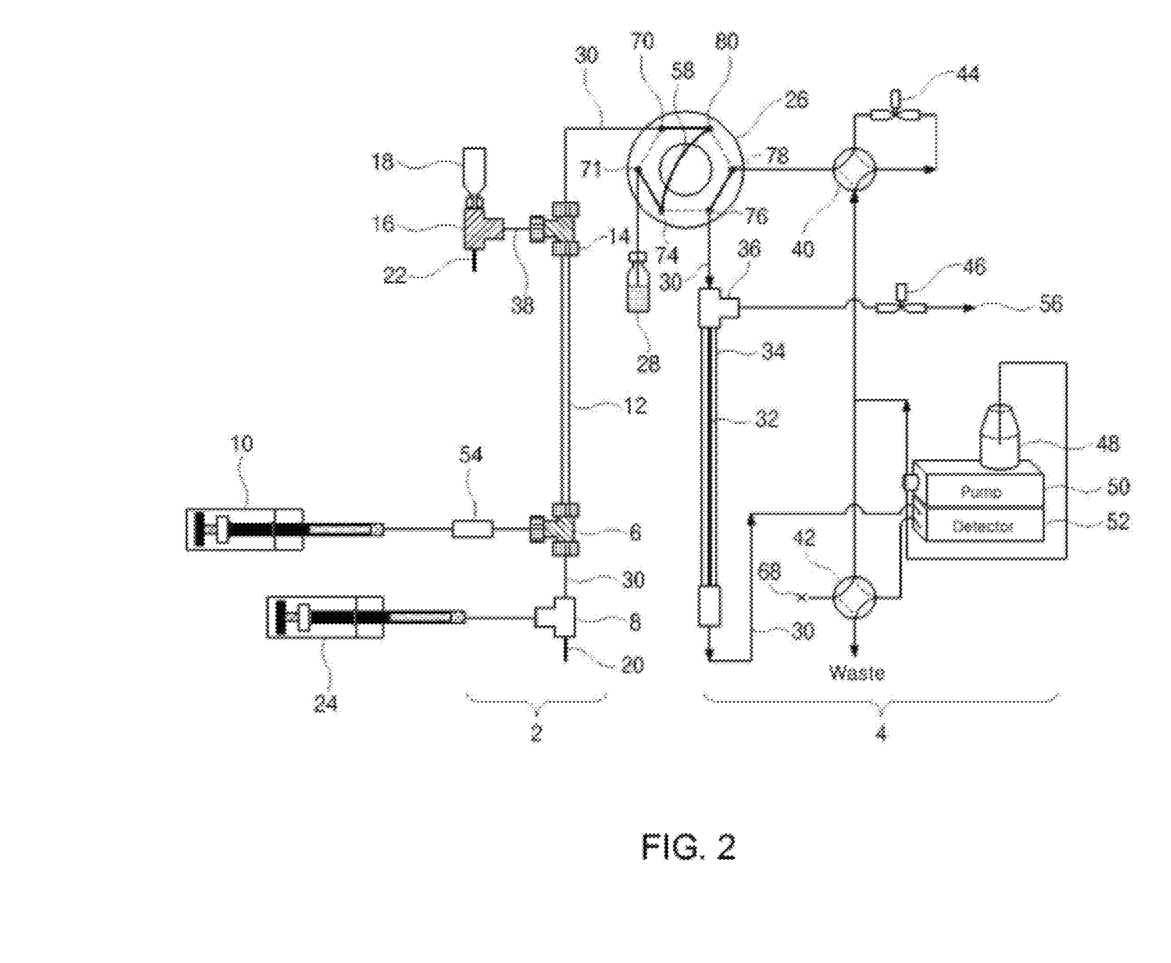

As a plan to overcome this problem, a 2D separation method, CIEF-Hollow fiber flow-field flow fractionation (HF FIFFF) has been developed, whereby isoelectric focusing and molecular weight based separation without using the gel are possible. The CIEF-HF FIFFF is configured to serially connect HF FIFFF with the CIEF method that carries out the isoelectric focusing in the capillaries, and more particularly, fills the ampholyte carriers in the silica capillaries along with the proteins, and applies the electric field to separate the proteins according to the pI of the protein [Conti, M.; Gelfi, C.; Righetti, P. G. *Electrophoresis* 1996, 17, pp. 1485-1491]. The HF FIFFF belongs to another example of separating and analyzing the proteins, and is a separation method that uses a hollow fiber membrane as a separation channel [W. J. Lee, B.-R. Min, M. H. Moon, *Anal. Chem.* 1999, 71(16), p. 3446; M. H. Moon, K. H. Lee, B.-R. Min, *J. Microcolumn* September, 1999, 11(9), p. 676; P. Reschiglian, et al. *Anal. Chem.* 2005, 77, p. 47]. In the HF FIFFF, the function of an external field is determined by the flow rate of a cross flow or a radial flow discharged to an outer wall of the hollow fiber membrane, and samples in the channel maintain an equilibrium with the external field. In this case, as shown in FIG. 2, the samples proceed in the shape of a circular band. At this time, a ratio of the flow of the samples to a separation flow moving toward a longitudinal axis of the channel is adjusted, thereby adjusting a separation speed.

The CIEF-HF FIFFF [D. Kang, M. Moon, *Anal. Chem.*, 2006, 78, pp. 5789-5798] has an advantage in that the proteins can be separated in two dimensions without using the gel, and a disadvantage in that an amount of separable proteins has no choice but is restricted due to a limitation of a capacity of the capillary in the event of the primary isoelectric focusing the capillary. Further, while a fraction of the proteins separated according to pI after the primary separation is transferred to a hollow fiber module, and then separated according to molecular weight, the other proteins stand by in the capillaries, and then are separated in the hollow fiber module. For this reason, a total separation time is prolonged by a desired fraction of pI. In addition, while some of the protein samples primarily separated according to pI are secondarily separated in the hollow fiber module according to the molecular weight, the other pI fractions must stand by in the capillaries under the electric field. In this process, the proteins are slightly shifted due to the influence of an electroosmotic flow driven on inner walls of the capillaries. This results in a problem that allows the separated fractions to be mixed again, and causes contamination of the fractions. In the case of the CIEF-HF FIFFF, because a maximum amount of the proteins that can be injected at once is about 40 μg, there is the limitation of a capacity to some extents to process a large amount of proteome samples.

Technical Problem

In order to solve the foregoing and/or other problems, it is an aspect of the present invention to provide a non-gel based protein separating and/or analyzing apparatus capable of reducing a time to separate proteins and increasing a rate of processing separated protein samples, and a method of manufacturing the same.

It is another aspect of the present invention to provide a protein separating and/or analyzing method using the non-gel based protein separating and/or analyzing apparatus.

Technical Solution

According to an aspect of the present invention, there is provided a protein separating apparatus, which includes at least one fluid channel having a predetermined length. The fluid channel is divided into an isoelectric focusing section that primarily separates proteins from protein samples according to pI, and a flow field-flow fractionation section that secondarily separates the primarily separated proteins according to molecular weight. The isoelectric focusing sections of the fluid channels are connected with each other.

According to another aspect of the present invention, there is provided a protein analyzing apparatus, which includes the protein separating apparatus according to the first aspect of the present invention, and a protein detector analyzing the proteins separated by the protein separating apparatus.

According to still another aspect of the present invention, there is provided method of separating proteins using the protein separating apparatus according to the first aspect of the present invention. The method includes: filling a pump with a mixture of the protein samples and an ampholyte solution, feeding the mixture to the isoelectric focusing section, applying an electric field to the isoelectric focusing section so as to isoelectrically focus the protein samples, and separating the proteins from the protein samples according to pI; and feeding the isoelectrically focused protein samples to a flow field-flow fractionation section, and separating proteins from the protein samples according to molecular weight.

According to yet another aspect of the present invention, there is provided a method of analyzing proteins, which includes separating the proteins using the method of separating method according to the third aspect of the present invention, and analyzing the separated proteins using a protein detector.

Advantageous Effects

As can be seen from the foregoing, it is possible to separate the proteins according to pI and molecular weight, be safe from denaturation of the protein in the process of protein separation, and automatically remove an ampholyte used for pI-based separation. When the separated and recovered proteins are subjected to enzymatic hydrolysis treatment, it is possible to directly use protein identification by applying nanoflow liquid chromatography-electrospray ionization-tandem mass spectrometry (LC-ESI-MS-MS) to peptide analysis.

DESCRIPTION OF DRAWINGS

FIG. 5 shows processes of separating proteins using a protein separating apparatus according to an embodiment of the present invention, in which FIG. 5A is for a sample injection process, FIG. 5B is for an isoelectric focusing process, FIG. 5C is for a relaxation-focusing process, and FIG. 5D is for a separation process of flow field-flow fractionation.

BEST MODE

Reference will now be made in detail to the embodiments of the present invention.

The present invention is directed toward providing a protein separating apparatus, which includes at least one fluid channel having a predetermined length. Each fluid channel is divided into two sections: an isoelectric focusing section that primarily separates proteins from protein samples according to isoelectric point (pI), and a flow field-flow fractionation section that secondarily separates the primarily separated proteins according to molecular weight. The isoelectric focusing sections of the fluid channels are connected with each other.

The protein separating apparatus of the present invention is characterized in that the proteins primarily separated according to pI of the protein can be secondarily separated and analyzed through multiple channels capable of simultaneously driving the flow field-flow fractionation sections that separate the primarily separated proteins according to order of molecular weight.

Thus, the protein separating apparatus of the present invention is a so-called isoelectric focusing-flow field-flow fractionation multi-channel apparatus, and may be called a multi-channel apparatus for non-gel based two-dimensional (pI and molecular weight) protein separation when characteristics of the protein separating apparatus are intended to be expressed intensively.

Further, the present invention has a feature that can naturally remove an ampholyte through a semi-permeable membrane installed on a multi-channel bottom in the process of carrying out flow field-flow fractionation because isoelectric focusing of the proteins is carried out in the multiple channels where the flow field-flow fractionation are carried out. Thus, even the protein samples separated through a conventional capillary isoelectric focusing technique do not require a separate re-analysis process for removing analysis obstacle factors caused by the ampholyte obtained together in the mass analysis process of the proteins, so that a time to carrying out the protein separation process can be reduced.

Further, the protein separating apparatus of the present invention does neither require a separate connection tube for transferring the samples after the isoelectric focusing because the isoelectric focusing and the molecular weight based separation are sequentially carried out in the multiple channels, nor use an organic solvent for the separation, thereby avoiding denaturation of the proteins when the protein samples are separated. The protein separating apparatus of the present invention can separate the protein samples to be analyzed according to pI and molecular weight regions, particularly in a liquid phase rather than in a gel phase using a combination of pI-based and molecular weight based separations, collect protein fractions of desired pI-molecular weight regions, and separate a large quantity of protein samples and proteins by increasing a processing rate as needed. In addition, in the process of carrying out molecular weight based separation on the proteins separated according to pI, protein bands of several pI regions can be independently and simultaneously subjected to the molecular weight based separation without waiting of the proteins of other pI regions when the molecular weight based separation is performed on the proteins of any pI region.

Reference will now be made in greater detail to the embodiments of the present invention, examples of which are illustrated in the accompanying drawings. The accompanying drawings are merely provided to describe the present invention in greater detail, and are not intended to limit the technical spirit of the present invention.

Figure 3:
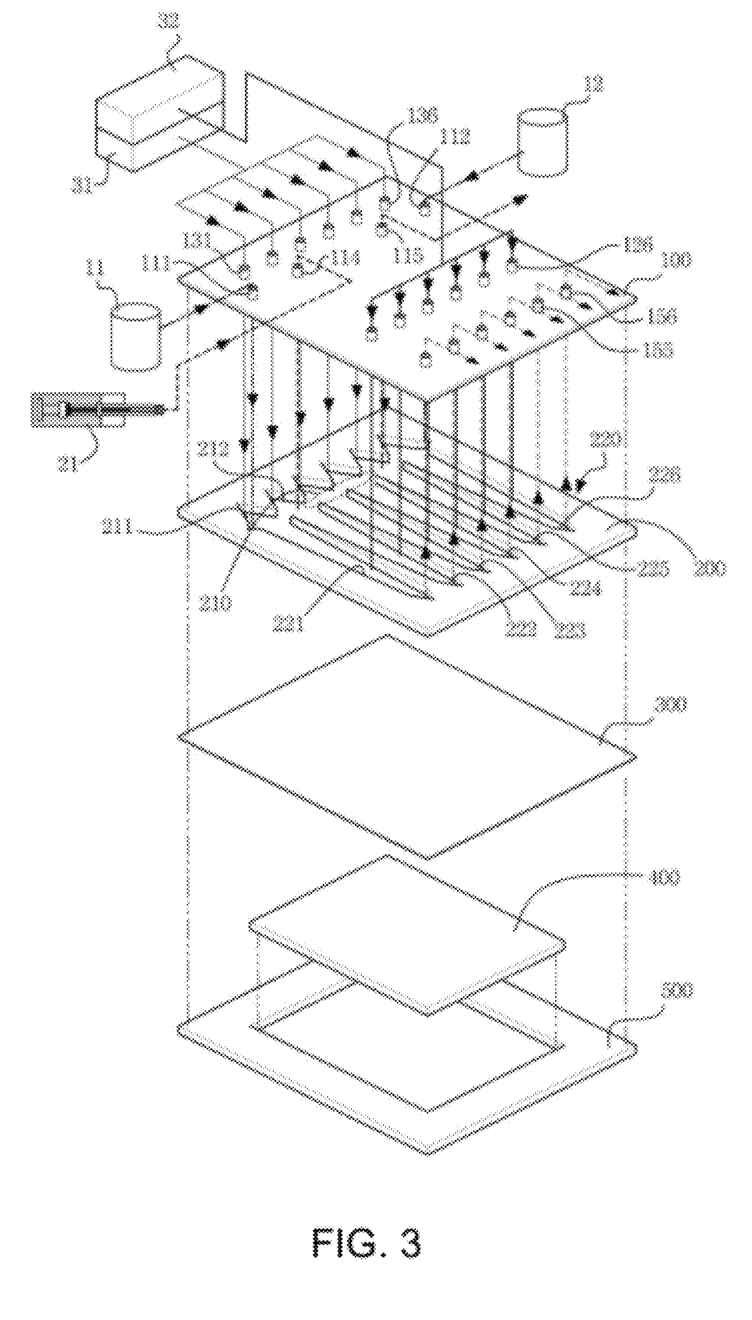
FIG. 3 shows the configuration of a protein separating apparatus according to an embodiment of the present invention.
Figure 4:
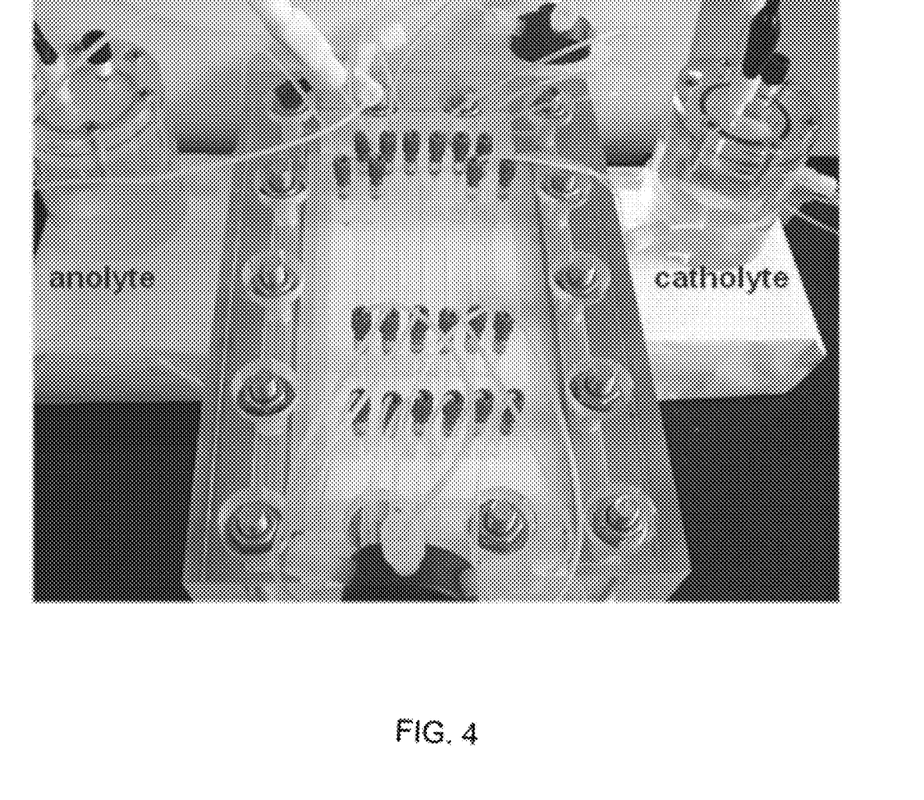
FIG. 4 is a photograph showing the connection of a protein separating apparatus according to an embodiment of the present invention.

FIG. 3 shows the configuration of a protein separating apparatus according to an embodiment of the present invention. FIG. 4 is a photograph showing the connection of a protein separating apparatus according to an embodiment of the present invention.

The protein separating apparatus according to an embodiment of the present invention includes at least one fluid channel having a predetermined length. Each fluid channel is divided into two sections: an isoelectric focusing section that primarily separates proteins from protein samples according to isoelectric point (pI), and a flow field-flow fractionation section that secondarily separates the primarily separated proteins according to molecular weight. The isoelectric focusing sections of the fluid channels may be connected with each other.

Further, the protein separating apparatus of the present invention includes a lower block 500, a membrane 300 disposed on the lower block, a spacer 200 disposed on the membrane and including at least one cutout part having a predetermined length, and an upper block 100 disposed on the spacer and fastened with the lower block. Each cutout part of the spacer serves as a fluid channel defined by the upper and lower blocks. Each fluid channel may be divided into the isoelectric focusing section connected with its neighboring fluid channel, and the flow field-flow fractionation section disconnected from its neighboring fluid channel.

The protein separating apparatus of the present invention further includes a sample feeder 21 feeding the protein samples to the fluid channels of the isoelectric focusing section, first and second electrolyte storages 11 and 12 feeding catholyte and anolyte to a boundary between the isoelectric focusing section and the flow field-flow fractionation section respectively, and pumps 31 and 32 feeding a buffer solution to the fluid channels of the isoelectric focusing section and the fluid channels of the flow field-flow fractionation section respectively.

The sample feeder 21 may include a syringe pump, and feeds a mixture of the protein samples and ampholyte into an inflow port 114 located on the left side of the isoelectric focusing section through a Teflon tube. Further, a solvent in the fluid channels is configured to be discharged to an outlet through an outflow port 115 located on the right side of the isoelectric focusing section such that the sample solution entering the sample feeder 21 is linearly distributed on the isoelectric focusing section.

Further, the electrolyte storages 11 and 12 are filled with catholyte and anolyte respectively, may be made of plastic, and include a cathode and an anode respectively.

The electrolyte storages 11 and 12 are connected with electrolyte inflow ports 111 and 112 located on opposite sides of the isoelectric focusing section through Teflon tubes, and carry out isoelectric focusing of the protein samples.

The cathode and anode are not substantially limited if they are electrodes typically used in the art, and may employ platinum electrodes.

In the protein separating apparatus of the present invention, the first and second feed pumps 31 and 32 for feeding the buffer solution are connected with a fluid storage in order to separate the proteins in the flow field-flow fractionation section according to molecular weight.

The first feed pump 31 is to feed a fluid, preferably a buffer solution, for separating the proteins according to molecular weight toward an inlet of the flow field-flow fractionation section, and is connected with fluid inflow ports 131 to 136 of the flow field-flow fractionation section through Teflon tubes.

The second feed pump 32 is to feed a fluid, preferably a buffer solution, for separating the proteins according to molecular weight toward a focusing flow part of the flow field-flow fractionation section, and is connected with focusing flow inflow ports 121 to 126 of the flow field-flow fractionation section through Teflon tubes.

The first feed pump 31 or the second feed pump 32 may use, but not substantially limited to, a high performance liquid chromatography (HPLC) pump.

Further, the buffer solution is not substantially limited if it is a typical buffer solution used for protein separation.

Further, the upper block includes the numerous inflow ports 131 to 136 and 121 to 126 and outflow ports 151 to 156, all of which are mounted at positions corresponding to the fluid channels. The inflow ports 131 to 136 connect the fluid channels with the sample feeder 21, the first and second electrolyte storages 11 and 12, and the pumps 31 and 32. The outflow ports 151 to 156 correspond to the fluid channels of the flow field-flow fractionation section.

One end of the isoelectric focusing section is spaced apart from the inlet of the flow field-flow fractionation section by a distance ranging from 0.2 cm to 2 cm. The isoelectric focusing sections of the fluid channels are constructed to be interconnected such that the proteins are subjected to isoelectric focusing separation.

The flow field-flow fractionation section may be constructed to fixedly mount a frit 400 in the lower block 500, and to be spaced apart from the frit 400, mounted in the lower block, with a gap where the fluid can maintain a pressure all over while being temporarily stored when flowing through. Thus, the frit 400 fixed to the lower block 500, the membrane 300, at least one spacer 200 forming the gap of the channel, and the upper block 100 are sequentially stacked and assembled.

A material of the lower block 500 is not substantially limited, but may use acryl or Lucite (transparent thermoplastic acrylic resin).

Further, the frit 400 of the protein separating apparatus of the present invention may be installed in the lower block 500 at a predetermined depth in order to pass a necessary cross flow when the proteins are separated, namely, such that a waste after the proteins are separated flows in through the membrane.

The frit 400 may use a permeable frit made by compression of ceramic particles.

A pore size of the frit may range from 1 $\mu$m to 10 $\mu$m in order to smoothly pass the cross flow.

Further, the membrane 300 is used for preventing a loss of the protein samples, and is not substantially limited if it is a semi-permeable membrane typically having a molecular weight cut-off size smaller than a minimum molecular weight of the protein sample. The membrane may include a polymeric membrane made of one or at least two of cellulose, polysulfone, and polypropylene, each of which has the molecular weight cut-off size between 10 kDa and 30 kDa.

Further, the spacer 200 may be fabricated in a shape of at least two cut-out ribbons, preferably two through twelve, having 210 pI based separation section, wherein the inlets of the fluid channels 211 and 212 are open to each other such that the isoelectric focusing occurs within a region ranging from 5% to 30% of the channel length.

The spacer 200 may have a thickness ranging from 50 $\mu$m to 500 $\mu$m in order to form a gap where the fluid can maintain a pressure all over while being temporarily stored when flowing through.

Further, in the protein separating apparatus of the present invention, the flow field-flow fractionation section of each fluid channel 221 has a trapezoidal structure having a width that is reduced from the inlet thereof to the outlet 222, 223, 224, 225, 226 thereof, or a rectangular structure having the same width, and may have a structure in which one or more channels having an inlet width ranging from 1 cm to 3 cm and an outlet width ranging from 0.3 cm to 3 cm are connected in parallel.

Further, the upper block has no frit, and is constructed to form the inflow ports 131 to 136 and 121 to 126 and the outflow port 151 to 156 for inflow and outflow of the fluid using a drill. Each port includes a connector for tube connection.

The upper block includes the fluid inflow ports 131 to 136 connected with the first feed pump 31, the inflow port 114 feeding the mixture of the protein samples and the ampholyte, the outflow port 115 discharging the solvent, the focusing flow inflow ports 121 to 126 connected with the second feed pump 32, the outflow ports 151 to 156 for the analyzed proteins, and the inflow ports 111 and 112 connected with the catholyte storage 11 and the anolyte storage 12 respectively.

The connector of each port which is used for the tube connection may use a union made of polyetheretherketone (PEEK).

The fluid inflow ports 131 to 136 or the focusing flow inflow ports 121 to 126 may be connected with the first feed pump 31 or the second feed pump 32 in a multi-way manifold type, i.e. in a type where one inlet is connected with two or more outlets.

Each port may be connected with the pump using a Teflon tube.

The inflow ports 111 and 112 connected with the electrolyte storages 11 and 12 may be provided with a semi-permeable membrane having 10 kDa or less in order to prevent the protein samples from reflowing to the electrolyte storages.

The semi-permeable membrane may include a polymeric membrane made of one or at least two of cellulose, polysulfone, and polypropylene.

The present invention is also directed toward providing a protein analyzing apparatus, which includes the protein separating apparatus and a protein detector analyzing the proteins separated by the protein separating apparatus.

The protein detector is connected with the protein outflow ports 151 to 156 of the upper block 100 through a Teflon tube below the fluid channels of the protein separating apparatus.

A type of the protein detector is not substantially limited if it is a typical detector used to analyze the separated proteins in the art, and may use an infrared detector.

Further, the protein analyzing apparatus of the present invention collects fractions of the proteins separated by the protein separating apparatus according to molecular weight range, converts the collected protein fractions into peptides through enzyme treatment, separates the peptides using nano-flow liquid chromatography-electrospray ionization-tandem mass spectrometry (LC-ESI-MS-MS), and identifies the proteins through comparison of a mass spectrum with a protein database. A fraction collector may be additionally connected to an outlet of the protein detector.

Further, the feed pumps, valves such as pressure valves, etc. constituting the protein separating apparatus may be connected to a computer so as to be controllable, and then the multi-channel outlets through which the separated proteins finally pass may be connected to an automatic fraction collector. In this case, the protein analyzing apparatus of the present invention may automatically separate the proteins according to pI and molecular weight, and connect the channel outlets with an electrospray ionization-mass spectrometer (ESI-MS) on line using capillaries, preferably silica capillaries.

The ESI-MS may be applied to protein identification because a structural analysis of protein chains is possible when the ESI-MS uses tandem mass analysis along with mass analysis of the proteins, and may automatically remove the ampholyte because the ampholyte introduced from the isoelectric focusing section in the process where the protein samples are separated in the multiple channels is discharged along with the cross flow during the sample relaxation-focusing and separation processes.

Further, in the components of each apparatus according to the present invention, the tubes used for movement paths, along which the protein samples, the electrolyte solution, and the buffer solution flow, are not substantially limited if they are tubes made of a material that does not react with the aforementioned substances and is typically used in the art, but may use Teflon tubes.

A method of manufacturing the protein separating apparatus according to an embodiment of the present invention will be described below in detail.

The frit 400 is fixed to the acryl or Lucite block 500, and the membrane 300, the spacer 200 forming the gap for the fluid channels, and the upper block 100 are sequentially stacked and assembled on the frit. Thereby, the fundamental framework of the multiple channels is formed.

A wall above the fluid channels, i.e. the upper block 100 has no frit, and includes fluid pathways formed by a drill for inflow and outflow of the fluid. The wall above the fluid channels is provided with connectors for tube connection. The fluid channels are based on a structure in which at least two ribbon-type multiple channels, preferably two through twelve ribbon-type multiple channels are connected in parallel. The multi-channel spacer 200 having a thickness ranging from 50 µm to 500 µm has a shape of multiple cut-out ribbons as in FIG. 3 in such a manner that the inlets of the fluid channels are open to each other such that the isoelectric focusing occurs within a region ranging from 5% to 30% of the channel length.

Each of the multiple channels is configured to have an inlet width ranging from 1 cm to 3 cm, an outlet width ranging from 0.3 cm to 3 cm, and a length of about 10 cm from a position past the isoelectric focusing section.

The isoelectric focusing section is spaced apart from the inlet of the flow field-flow fractionation section by a distance ranging from 0.2 cm to 2 cm. The isoelectric focusing section is connected to the electrolyte storages 11 and 12, which are filled with the catholyte and anolyte respectively, through a Teflon tube. The electrolyte storages 11 and 12 are connected by platinum electrodes, particularly a cathode and an anode, respectively.

The fundamental framework of the multiple channels and the upper block 100 is fastened with bolts.

The present invention is also directed toward providing a method of separating proteins using the protein separating apparatus defined in claim 1. The protein separating method includes: a process of filling a pump with a mixture of the protein samples and an ampholyte solution, feeding the mixture to the isoelectric focusing section, applying an electric field to the isoelectric focusing section so as to isoelectrically focus the protein samples, and separating the proteins from the protein samples according to pI; and a process of feeding the isoelectrically focused protein samples to a flow field-flow fractionation section, and separating proteins from the protein samples according to molecular weight.

Figure 5:
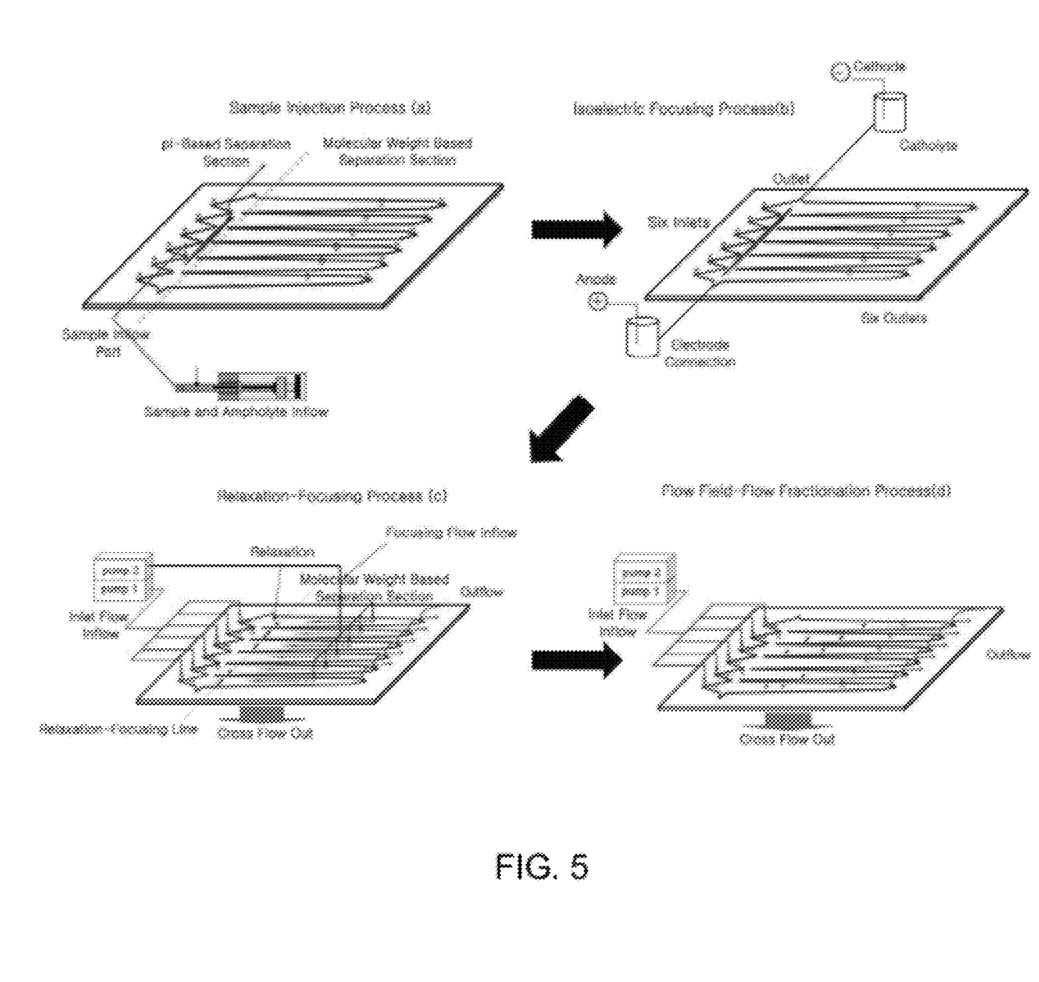

The process of separating proteins according to pI is configured to fill the syringe pump 21 with the mixture of the protein samples to be separated and analyzed and the ampholyte solution, and to inject the mixture to the sample inflow port 114 through the connector connected by the Teflon tube on the left side of the isoelectric focusing section (sample injection process) (see FIG. 5A).

The protein samples are not substantially limited, and may use one or at least two selected from myoglobin, trypsinogen, carbonic anhydrase, bovine serum albumin, cytochrome-c, apoferritin, or yeast alcohol dehydrogenase, etc.

The ampholyte solution may have pH ranging from 3 to 10 and a concentration ranging from 0.5% to 3%.

The ampholyte solution is not substantially limited if it is typically used for the isoelectric focusing in the art.

Further, the concentration of the ampholyte solution means a volumetric proportion which the ampholyte solution occupies in a sample solution fed to the sample feeder. When the concentration of the ampholyte solution is less than 0.5%, it is difficult to form an exact pH gradient due to shortage of buffer capacity of the ampholyte solution, so that pI-based separation hardly occurs. When the concentration of the ampholyte solution is more than 3%, excessive ampholyte molecules are shifted by electric force, so that movement of protein molecules is relatively reduced. When the concentration of the ampholyte solution increases, viscosity of the ampholyte solution increases to inhibit molecular movement because the ampholyte solution has a higher viscosity than water. Thus, the concentration of the ampholyte solution may be most preferably set to 1% so as to be able to maintain the buffer capacity and avoid inhibiting the movement of the protein molecules.

The ampholyte solution may have a content ranging from 1 to 2 parts by weight on the basis of 100 parts by weight of the protein samples. When the content of the ampholyte is less than 1 part by weight, it takes much time to form the pH gradient to carry out the pI-based separation, and the buffer capacity of the ampholyte solution becomes insufficient. When the content of the ampholyte is more than 2 parts by weight, the number of ampholyte molecules is relatively excessive compared to the number of protein molecules, and thus inhibits the movement of the protein molecules.

Further, the process of isoelectrically focusing the protein samples is configured to apply the electric field ranging from 0.1 kV/cm to 1 kV/cm to the isoelectric focusing section into which the mixture of the protein samples and the ampholyte solution is injected for a time ranging form 1 min to 20 min so as to isoelectrically focus the protein samples, and release the electric field after the pI-based separation is completed (isoelectric focusing process) (see FIG. 5B).

The stronger the strength of the applied electric field, the shorter the time for the pI-based separation. However, when the electric field applied is too strong, a large quantity of heat is generated, and bubbles are generated in the tube connecting the catholyte with the channel, so that a flow of current is interrupted. Thus, the applied electric field may range from 0.1 kV/cm to 1 kV/cm, and preferably 100 V/cm to 600 V/cm.

The process of separating the proteins according to molecular weight is configured to drive the first feed pump 31 connected to one side of the fluid storage, feed a buffer solution stored in the fluid storage to the fluid inflow ports 131 to 136 of the channel inlets and the focusing flow inflow ports 121 to 126, and move protein fractions to the neighboring multiple channels (see FIG. 5B) with equilibrium maintained on a sample relaxation-focusing line through regulation of a flow rate.

When the isoelectric focusing is completed, the fluid is fed to the fluid inflow ports 131 to 136 and the focusing flow inflow ports 121 to 126 of the multiple channels. A flow rate ratio is regulated such that the bands of the protein samples undergoing the isoelectric focusing separation are injected into the corresponding channels at different flow rates and then are focused on a position of the sample relaxation-focusing line shown in FIG. 5C (about 0.5 cm from the isoelectric focusing section), and a relaxation process is carried out for a time when the samples can reach an equilibrium state through a sufficient relaxation process (i.e. for a time when the fluid ranging from about one to three times the channel volume can be discharged in a cross flow) (relaxation-focusing process) (see FIG. 5C).

Further, for the sample relaxation process, the samples may be focused at a position ranging from 10% to 50% of the entire channel length (i.e. from a position where the isoelectric focusing is terminated to the channel outlet). To this end, the flow rates of the fluids, one of which is fed through the fluid inflow ports 131 to 136 and the other the focusing flow inflow ports 121 to 126 of the multiple channels, are regulated to a ratio ranging from 1:9 to 5:5. The samples are focused in the equilibrium state at a position ranging from 10% to 50% of the entire channel length, preferably at a position of 10% of the entire channel length. Simultaneously, both the buffer solution flowing into the multiple channels and the ampholyte used for the isoelectric focusing are discharged out of the membrane along the pores of the membrane.

Further, a volume of the proteins undergoing the isoelectric focusing in the aforementioned process is adjusted to a range from 1 μl to 70 μl, preferably about 10 μl, so as to correspond to the size of a desired pI region. Here, when the ampholyte used ranges from pH 3 to pH 10, any one of the multiple channels corresponds to 1/6, and thus a pI interval corresponds to a 1.17 pI interval Further, after the equilibrium is maintained in the aforementioned process, the buffer solution of the fluid storage is fed only to the fluid inflow ports 131 to 136 of the multiple channels, so that the proteins are separated in order from low molecular weight to high molecular weight using the flow field-flow fractionation.

When the relaxation-focusing of the samples is completed, the fluid fed to the focusing flow inflow ports 121 to 126 is blocked, and simultaneously the flow rate of the fluid fed by the first feed pump 31 is raised up to the flow rate required for separation. Then, the fluid is fed only to the fluid inflow ports 131 to 136 of the channel inlets at a flow rate that corresponds to a sum of that of the cross flow and that of the outlet flow. At this time, it does not matter that the focusing flow inflow ports 121 to 126 are left without any measure when they are disconnected from or connected with the pump using valves. In this process, the proteins are separated in order of molecular weight, and are discharged to the outlets of the respective channels (separation process) (see FIG. 5D).

The present invention is also directed toward providing a method of analyzing proteins. This method includes a process of separating the proteins using the protein separating method, and a process of analyzing the separated proteins using a protein detector.

The proteins may be analyzed by connecting the protein separating apparatus to the protein detector or by collecting fractions of eluted proteins according to time or at a desired time interval using a fraction collector.

Further, the proteins may be analyzed by connecting the fraction collector to a downstream end of the protein separating apparatus.

When the fraction collector is connected to the detector, the protein fractions may be collected according to molecular weight range. Further, the collected protein fractions may be converted into peptides through enzyme treatment. The peptides may be separated using nanoflow liquid chromatography-electrospray ionization-tandem mass spectrometry (LC-ESI-MS-MS), and then the proteins may be identified through comparison of a mass spectrum with a protein database.

Further, the proteins may be analyzed by connecting the protein outflow ports 151 to 156 of the protein separating apparatus of the present invention to an electrospray ionization-mass spectrometer (ESI-MS) using capillaries.

The injection pump, feed pumps, valves such as pressure valves, etc. constituting the protein separating apparatus may be connected to a computer so as to be controllable, and then the multi-channel outlets through which the separated proteins finally pass may be connected to an automatic fraction collector. In this case, the proteins may be automatically separated according to pI and molecular weight, and the channel outlets may be connected with the ESI-MS on line using capillaries, preferably silica capillaries.

Further, when the ESI-MS uses tandem mass analysis along with mass analysis of the proteins, the ESI-MS may be applied to protein identification because a structural analysis of protein chains is possible, and may automatically remove the ampholyte because the ampholyte, which is introduced from the isoelectric focusing section in the process where the protein samples are separated in the multiple channels, is discharged along with the cross flow during the sample relaxation-focusing and separation processes.

The proteome can be analyzed from the separated protein samples using one of the aforementioned methods.

MODE FOR INVENTION

Reference will now be made in detail to the embodiments of the present invention. However, the following embodiments are merely illustrative of the present invention, and thus the disclosure of the present invention is not limited to the following embodiments.

Example 1

Manufacturing of Protein Separating Apparatus

In order to connect the multiple channels with the tubes, a total of 22 connectors, i.e. six inlets and six outlets, six connectors for discharging the fluid from the six focusing flow parts, two connectors for inflow and outflow of the samples and two connectors for connection with the electrodes within the isoelectric focusing section, employed nuts of the same PEEK (available from Upchurch Scientific, USA), as shown in FIG. 4. The six Teflon tubes of the channel inlets were connected with the first feed pump using a 6-way manifold (having one inlet and six outlets) (available from Upchurch Scientific, USA). The first feed pump employed an HPLC pump. Similarly, the focusing flow inlets for the focusing flow (the six inlets between the channel inlets and the channel outlets) were connected with the second feed pump using Teflon tubes and a 6-way manifold in the same fashion as the channel inlets. The six connectors of the channel outlets employed nuts of the same PEEK. Here, in the case of the channel outlets, in order to control flow rates of a cross flow and an outlet flow, outlet connection tubes were put under pressure by adjusting the length of a silica capillary (inner diameter of 75 μm and outer diameter of 360 μm), and were simultaneously connected to a detector (available from Young-Lin Instruments, Korea, under the name of M720). Next, the detector was connected with a fraction collector at an outlet thereof, thereby recovering separated proteins according to time zone. In order to discharge the cross flow through one outlet of the channel bottom, this outlet was also connected using the Teflon tube and the connector of PEEK.

One of the two connectors of the isoelectric focusing section of the multiple channels was connected with a syringe pump (available from Harvard Apparatus, USA, under the name of Harvard Apparatus 22) using a Teflon tube. The syringe pump was filled with protein samples including myoglobin (15 kDa, pI 6.8), trypsinogen (24 kDa. pI 9.3), carbonic anhydrase (29 kDa, pI 5.85), bovine serum albumin (BSA, 66 kDa, pI 4.8), and yeast alcohol dehydrogenase (YADH) (150 kDa. pI 6.23), and an ampholyte solution ranging from pH 3 to pH 10 (available from Fluka, Switzerland). The Teflon tube was connected with the channel using a nut of PEEK (available from Upchurch Scientific, USA).

Next, electrodes were connected on opposite sides of the isoelectric focusing section. Here, the electrodes were platinum electrodes, submerged in plastic electrolyte storages in which catholyte and anolyte solutions were stored, and thus were connected from the respective electrolyte storages to the opposite sides of the isoelectric focusing section through respective Teflon tubes. Here, the electrolyte storages were Cross electrolyte storages (available from Upchurch Scientific, USA), one of which was filled with the anolyte solution, 20 mM $H_3PO_4$ solution made of ultrapure water (>18MΩ) filtered by a 0.22 μm separation membrane filter, and the other the catholyte solution, 20 mM NaOH solution made of ultrapure water (>18MΩ) filtered by a 0.22 μm separation membrane filter. The Teflon tube and the channel were connected using a nut of PEEK, and a small membrane (molecular weight cut-off size of 10 kDa) was interposed between the nut and the channel so as to prevent the proteins from moving to the electrode, i.e. out of the channel. The electrodes of platinum were directly installed on the plastic containers, and then were connected with a power supply.

Next, the two HPLC pumps were connected on one side of a fluid storage (5 L Erlenmeyer flask, available from Schott Duran, Germany) filled with a buffer solution. Thereby, the protein separating apparatus was completely manufactured.

Example 2

Separation of Single Protein Standard Substance Using Isoelectric Focusing Apparatus In order to check an isoelectric focusing effect in the protein separating apparatus (isoelectric focusing-flow field-flow fractionation multi-channel apparatus) manufactured according to the Example 1, a sample, cytochrome-c (12.7 kDa, pI 10.25), was separated by itself, and was mixed with an excessive amount (30 μg) of ampholyte solution in order to visually check a red color of the sample itself. The mixture was injected to the multiple channels using the syringe pump, and then was subjected to isoelectric focusing under the conditions of 3 min, 2 kV, and 1.25 mA.

Figure 6:
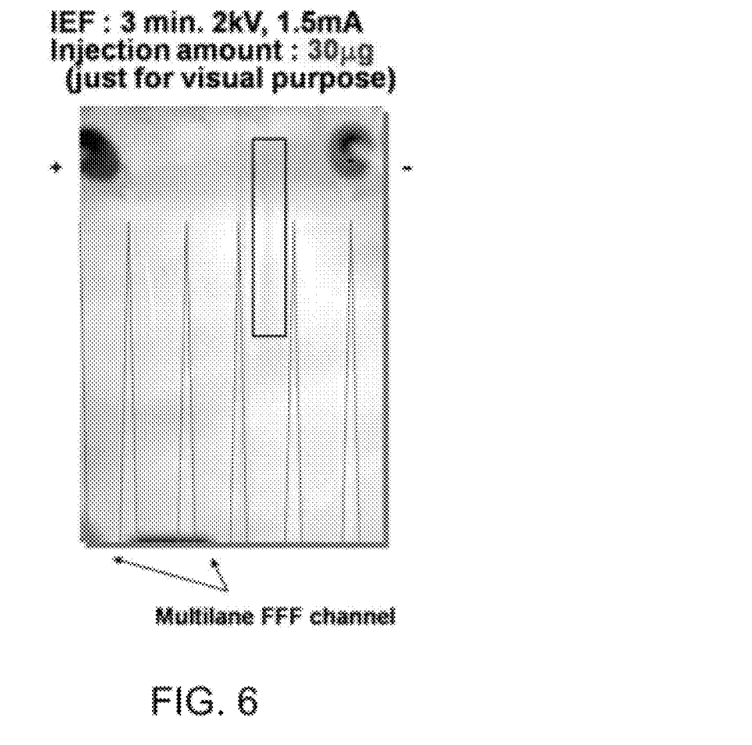
FIG. 6 shows results of isoelectrically focusing a single protein sample, cytochrome-c, using a protein separating apparatus according to an embodiment of the present invention.

As shown in FIG. 6, it can be seen that protein bands are indicated by narrow lines. In FIG. 6, the left side is an anode side, and the right side is a cathode side.

Further, the isoelectrically focused protein samples become electrically neutral between the opposite electrodes, are no longer electrophoresed toward the electrodes at a position where a pI region of the protein is equal to a pH value of the ampholyte around the protein, and form bands with thin lines. This is the principle of the isoelectric focusing. In FIG. 6, it can be found that despite injection of the excessive amount of samples, a band width of the samples is maintained narrow. However, the samples, which are injected at an excessive amount and are electrophoresed from the opposite sides up to an isoelectric point, are diffused toward the channel inlets and outlets, and thus form long bands. This does not matter in the case of the multiple channels. In detail, after the isoelectric focusing is completed, the samples are shifted toward the six channels on the lower side of FIG. 6 for the molecular weight based separation using the flow field-flow fractionation, and are again focused on a transverse axis (FIG. 6) at the inlet positions of the multiple channels (portions where the six channels are started) through a sample relaxation-focusing process. For this reason, the downward diffusion does not matter.

Example 3

Isoelectric Focusing Difference of Single Protein Caused by Voltage Change in the Event of Isoelectric Focusing The efficiency of the isoelectric focusing separation depending on a difference in applied voltage in the isoelectric focusing process using the protein separating apparatus of the Example 1 was examined. A sample, carbonic anhydrase (29 kDa, pI 5.8), was injected at an amount of 1 μg, and was subjected to the isoelectric focusing under the condition that the applied voltage was 1.0 kV, 2.0 kV, 2.5 kV, and 3.0 kV. The results of comparing the conditions of 1.0 kV and 3.0 kV are shown in FIG. 7.

Figure 7:
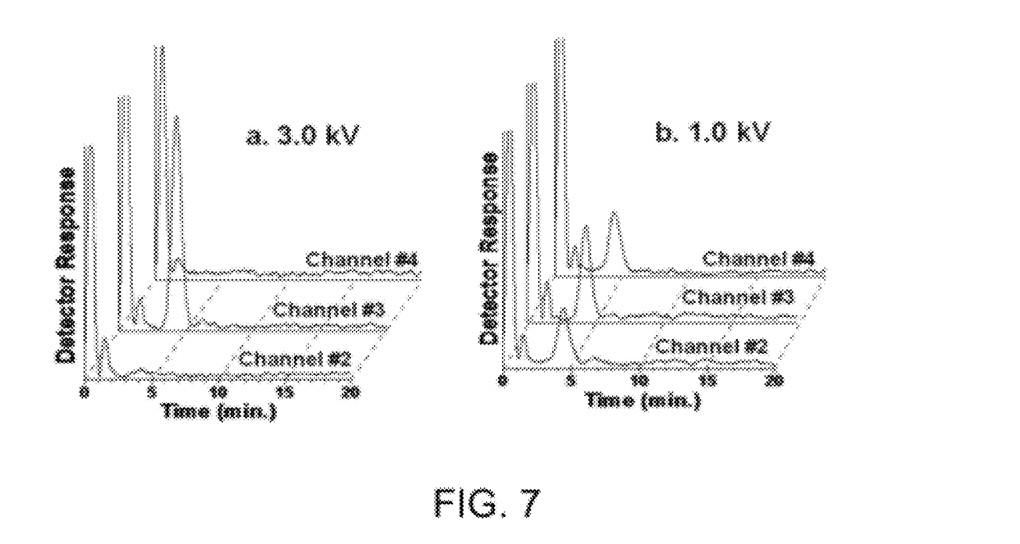
FIG. 7 shows results of isoelectrically focusing a single protein sample, carbonic anhydrase, on the basis of a change in voltage using a protein separating apparatus according to an embodiment of the present invention.

As shown in FIG. 7, when the applied voltage was 3.0 kV, a sample of carbonic anhydrase was focused within a given time, and was separated only in channel #3. In contrast, when the applied voltage was 1.0 kV, the protein was separated in channels #2, #3 and #4. This means that, when the protein is subjected to the isoelectric focusing, the protein is widely spread without forming the narrow bands as in FIG. 6, and that the protein is sufficiently focused within 100 seconds. On the other hand, when the applied voltage was 2.5 kV, the bovine serum protein was focused within a given time, and was separated in channel #2 but not channel #3. It can be seen from these tests that using 2.5 kV or more as the voltage applied for the isoelectric focusing is effective.

Example 4

Protein Isoelectric Focusing Difference Caused by Ampholyte Concentration Difference The efficiency of the isoelectric focusing separation depending on a difference in concentration of an ampholyte used in the isoelectric focusing process using the protein separating apparatus of the Example 1 was examined.

Figure 8:
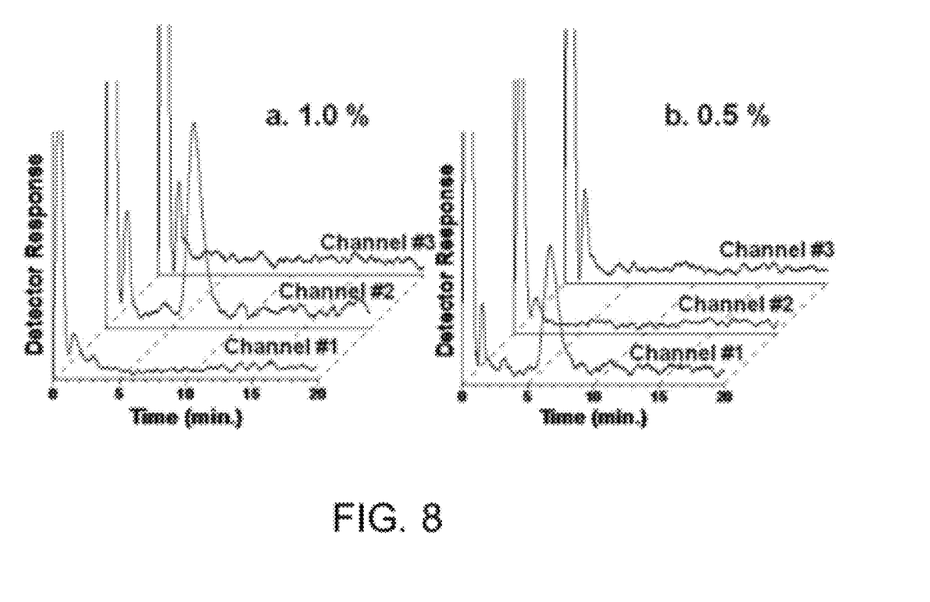
FIG. 8 shows results of isoelectrically focusing a single protein sample, bovine serum albumin, on the basis of a change in concentration of an ampholyte fed along with the sample using a protein separating apparatus according to an embodiment of the present invention.

It is shown in FIG. 8 that, in the case where a sample, bovine serum albumin (BSA) (66 kDa, pI 4.8), was injected and separated at an amount of 1 μg, a difference in separation efficiency was represented when a concentration of the mixed ampholyte when a protein sample solution was injected at an amount of 20 μl was 1% and 0.5%. The concentration means a volumetric proportion which the ampholyte occupies in a sample solution.

As shown in FIG. 8, when the concentration of 10% was used, the BSA was completely separated in channel #3. In contrast, when the concentration of 0.5% was used, a pH gradient of the ampholyte was insufficiently formed, and thus the sample protein was separated in channel #1 corresponding to the lowest pH region despite using the ampholyte solution ranging from pH 3 to pH 10. It can be seen from these tests that the concentration of 0.5% is not suitable.

Example 5

Separation of Protein Mixture Standard Substance Using IEF-FIFFF Apparatus

In order to check separation capability of the protein separating apparatus (isoelectric focusing-flow field-flow fractionation multi-channel apparatus) manufactured according to the Example 1, three types of protein standard substances were mixed to prepare a protein mixture sample. Here, the mixture of the protein standard substances had a composition as in Table 1.

TABLE 1

Composition of Mixture of Protein Standard Substances

| Type | Component | Property | Content (μg) |
|---|---|---|---|
| 1 | Carbonic Anhydrase | 29 kDa, pI 5.8 | 1 |

TABLE 1-continued

Composition of Mixture of Protein Standard Substances

| Type | Component | Property | Content (μg) |
|---|---|---|---|
| 2 | Bovine Serum Albumin | 66 kDa, pI 4.8 | 1 |
| 3 | Yeast Alcohol Dehydrogenase | 150 kDa, pI 6.2 | 1 |
| 4 | Apoferritin | 444 kDa, pI 5.4 | 1 |

A mixture solution of the protein mixture having the composition of Table 1 and an ampholyte (1%, v/v) was charged into a syringe pump of the protein separating apparatus manufactured according to the Example 1, and the syringe pump was driven to feed the mixture solution to Teflon capillaries. Then, an electric field of 357 V/cm was applied for about 1.5 minutes to isoelectrically focus the mixture solution, and then the first and second feed pumps were driven so as to allow protein samples to move from the isoelectric focusing section to the six channels. At this time, a ratio between flow rates was regulated such that the proteins were focused on inlets of the six channels, and the electric field was released.

The samples were divided and moved to the six channels, i.e. pI regions between 3 and 4.17, between 4.17 and 5.33, between 5.33 and 6.5, between 6.5 and 7.67, between 7.67 and 8.83, and between 8.83 and 10, and were used for flow field-flow fractionation separation. At this time, as in FIG. 5C, a flow of the solution was designed so that a part of the focusing flow moved to the sample relaxation-focusing line, and the other channel outlets. This was for reducing fluctuation of a bottom line of the detector by causing the detector to maintain the flow at a predetermined flow rate. Further, a part of the buffer solution was fed up to the sample relaxation-focusing line through the channel inlets, and was discharged through the membrane of the channel bottom in a cross flow along with the ampholyte used for the isoelectric focusing.

The sample relaxation-focusing was maintained for a time when the solution ranging from one to three times the entire volume of the channel was discharged in the cross flow perpendicular to a direction of the channel bottom, particularly for 90 seconds in this embodiment. At this time, the cross flow used amounted to 9.6 mL/min. For the flow field-flow fractionation just after the sample relaxation-focusing was completed, the focusing flow feed from the second feed pump was interrupted, and the buffer solution amounting to 10.0 mL/min was fed from the first feed pump only to the channel inlets (FIG. 5D). At this time, the flow rate of the cross flow used 9.6 mL/min as in the sample relaxation-focusing process, and the flow rate passing through each of the six channel outlets became 0.067 mL/min.

Figure 9:
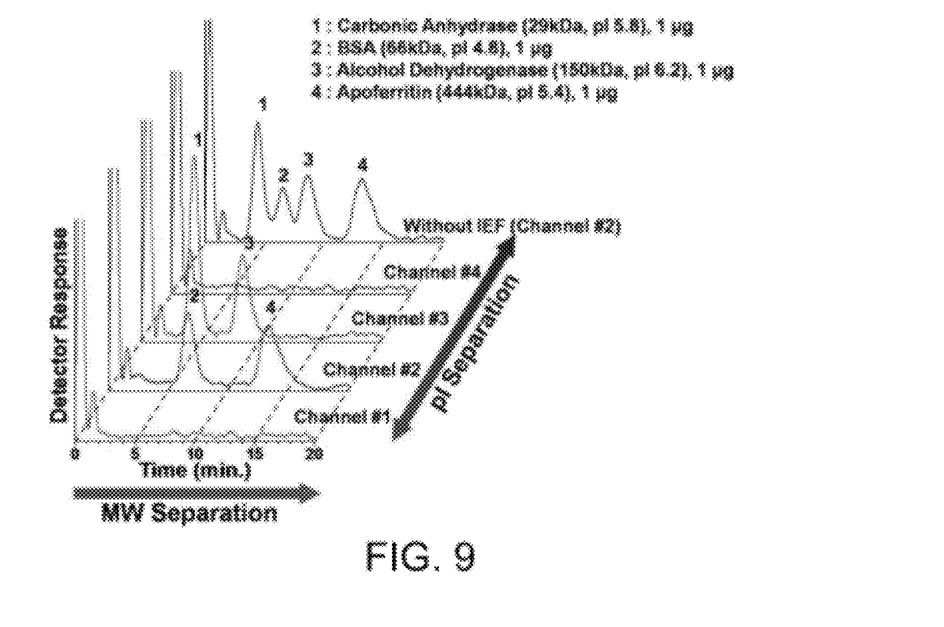
FIG. 9 shows results of isoelectrically focusing mixed protein samples using a protein separating apparatus according to an embodiment of the present invention.

The proteins, which were subjected to pI-based separation in this process and were introduced into each channel, were separated according to order of size, i.e. molecular weight. The results are shown in FIG. 9.

At this time, lane 1 refers to channel #1. Lane 1 has no protein of the corresponding pI region (between 3.0 and 4.17). Channel #2 has BSA (pI 4.8) and apoferritin, and channel #3 has carbonic anhydrase and yeast alcohol dehydrogenase. Channels #4, #5 and #6 have no protein of the corresponding pI region. Thus, the corresponding proteins seem to be separated in the two channels. In the case of channel #3, the proteins capable of being separated in the corresponding channel may be estimated to have the pI region between 5.5 and 6.5. In the case of apoferritin shown in FIG. 9 at present, pI is 5.4. Despite a slightly higher pI value than a boundary, apoferritin is not partially shown in channel #2. Thus, it can be estimated that accuracy of the isoelectric focusing of each channel of the present invention is very high. In the event of initial separation, a void peak appears in each lane just after the separation is started. This generally occurs at the flow field-flow fractionation apparatus. The cause of the void peak has not been determined in detail, but the void peak is responsible for a pressure change, etc. caused by a flow rate change occurring when the separation is started just after the sample relaxation-focusing. The pI value of each protein is included in a corresponding pH range which each channel may have. This can be seen from the fact that the proteins are successively subjected to the isoelectric focusing separation in the isoelectric focusing section and then the molecular weight based separation in the flow field-flow fractionation multiple channels.

INDUSTRIAL APPLICABILITY

The present invention provides a non-gel based protein separating apparatus capable of reducing a time to separate the proteins and increasing a rate of processing the separated protein samples, thereby being useful in protein purification applications.

What is claimed is:

1. A protein separating apparatus comprising:
    a spacer comprising a cutout portion comprising two or more fluid channels, wherein the fluid channels are divided into an isoelectric focusing section that first separates proteins from protein samples according to pI wherein the isoelectric focusing section is connected with a neighboring fluid channel thereof, and a flow field-flow fractionation section that secondarily separates the primarily separated proteins according to molecular weight, wherein the flow field-flow fractionation section is disconnected from a neighboring fluid channel.

2. The protein separating apparatus according to claim 1, further comprising:
    a lower block;
    a membrane disposed on the lower block;
    a the spacer disposed on the membrane and
    an upper block disposed on the spacer and fastened with the lower block,
    wherein each cutout part of the spacer has a fluid channel defined by the upper and lower blocks.

3. The protein separating apparatus according to claim 2, further comprising:
    a sample feeder feeding the protein samples to the fluid channels of the isoelectric focusing section,
    first and second electrolyte storages feeding catholyte and anolyte to a boundary between the isoelectric focusing section and the flow field-flow fractionation section, respectively; and
    pumps feeding a buffer solution to the fluid channels of the isoelectric focusing section and the fluid channels of the flow field-flow fractionation section, respectively.

4. The protein separating apparatus according to claim 2, wherein the upper block includes numerous inflow and outflow ports, all of which are mounted at positions corresponding to the fluid channels, the inflow ports connecting the fluid channels with the sample feeder, the first and second electrolyte storages, and the pumps, the outflow ports corresponding to the fluid channels of the flow field-flow fractionation section.

5. The protein separating apparatus according to claim 1, wherein the isoelectric focusing section is configured so that one end thereof is spaced apart from an inlet of the flow field-flow fractionation section by a distance ranging from 0.2 cm to 2 cm.

6. The protein separating apparatus according to claim 2, wherein the upper and lower blocks are made of acryl or Lucite.

7. The protein separating apparatus according to claim 2, wherein the lower block includes a frit installed at a depth ranging from 1 μm to 10 μm such that a waste after the proteins are separated flows in through the membrane.

8. The protein separating apparatus according to claim 2, wherein the membrane is a semi-permeable membrane having a molecular weight cut-off size ranging from 10 kDa to 30 kDa.

9. The protein separating apparatus according to claim 2, wherein the membrane is made of at least one selected from the group consisting of cellulose, polysulfone, and polypropylene.

10. The protein separating apparatus according to claim 2, wherein the spacer has a thickness ranging from 50 μm to 500 μm.

11. The protein separating apparatus according to claim 1, wherein each fluid channel constituted of the flow field-flow fractionation section has an inlet width ranging from 1 cm to 3 cm and an outlet width ranging from 0.3 cm to 3 cm.

12. The protein separating apparatus according to claim 4, wherein the inflow ports connected with the electrolyte storages further include a semi-permeable membrane having 10 kDa or less in order to prevent the protein samples from escaping.

13. A protein analyzing apparatus comprising:
    the protein separating apparatus according to claim 1; and
    a protein detector analyzing the proteins separated by the protein separating apparatus.

14. The protein analyzing apparatus according to claim 13, further comprising a fraction collector, which is connected to the outflow ports of the protein separating apparatus.

15. The protein analyzing apparatus according to claim 13, further comprising an electrospray ionization-mass spectrometer connected to the outflow ports of the protein separating apparatus.

16. A method of separating proteins using the protein separating apparatus according to claim 1, comprising:
    filling a pump with a mixture of the protein samples and an ampholyte solution, feeding the mixture to the isoelectric focusing section, applying an electric field to the isoelectric focusing section so as to isoelectrically focus the protein samples, and separating the proteins from the protein samples according to pI; and
    feeding the isoelectrically focused protein samples to a flow field-flow fractionation section, and separating proteins from the protein samples according to molecular weight.

17. The method according to claim 16, wherein the protein sample includes at least one selected from the group consisting of myoglobin, trypsinogen, carbonic anhydrase, bovine serum albumin, cytochrome-c, apoferritin, and yeast alcohol dehydrogenase.

18. The method according to claim 16, wherein the ampholyte solution has a concentration ranging from 0.5% to 3% within a range from pH 3 to pH 10.

19. The method according to claim 16, wherein the ampholyte solution has a content ranging from 1 to 2 parts by weight on a basis of 100 parts by weight of the protein samples.

20. The method according to claim 16, wherein the separating of the proteins according to molecular weight is configured to drive the first feed pump connected to one side of the fluid storage, feed a buffer solution stored in the fluid storage to the fluid inflow ports, and feed bands of the separated proteins to the flow field-flow fractionation section, or drive the second feed pump to feed the buffer solution to focusing flow inflow ports, and maintain sample relaxation-focusing and equilibrium.

21. The method according to claim 20, wherein the fluids fed through the fluid inflow ports and the focusing flow inflow ports of the flow field-flow fractionation section have a flow rate ratio ranging from 1:9 to 5:5.

22. The method according to claim 20, wherein the fluids fed through the fluid inflow ports and the focusing flow inflow ports of the flow field-flow fractionation section are focused and balanced at a position ranging from 10% to 50% of an entire length corresponding to a sum of the isoelectric focusing section and the flow field-flow fractionation section.

23. The method according to claim 16, wherein the separating of the proteins according to molecular weight is configured to interrupt the fluid of the second feed pump after the relaxation-focusing and equilibrium of the samples are completed, to cause the buffer solution of the fluid storage to be fed only to the fluid inflow ports through the first feed pump, and separate the proteins in an order from a high molecular weight to a lower molecular weight using flow field-flow fractionation.

24. A method of analyzing proteins comprising:
separating the proteins according to claim 16; and
analyzing the separated proteins using a protein detector.

25. The method according to claim 24, further comprising connecting the outflow ports of the protein separating apparatus to an electrospray ionization-mass spectrometer using capillaries to analyze the proteins.

26. The method according to claim 24, further comprising recovering the protein samples separated from the protein separating apparatus to analyze proteomes.

* * * * *